(12) United States Patent
Galvagni et al.

(10) Patent No.: US 10,047,094 B1
(45) Date of Patent: Aug. 14, 2018

(54) PROCESS FOR THE PREPARATION OF TRIAZOLE AND SALT THEREOF

(71) Applicant: F.I.S.—FABBRICA ITALIANA SINTETICI S.P.A., Montecchio Maggiore (VI) (IT)

(72) Inventors: Marco Galvagni, Verona (IT); Ennio Grendele, Valdagno (IT); Giovanni Lora, Cornedo Vicentino (IT)

(73) Assignee: F.I.S.—FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 15/429,278

(22) Filed: Feb. 10, 2017

(51) Int. Cl.
*C07D 487/04* (2006.01)
*A61K 31/4985* (2006.01)
*C12P 7/26* (2006.01)

(52) U.S. Cl.
CPC ........ *C07D 487/04* (2013.01); *A61K 31/4985* (2013.01); *C12P 7/26* (2013.01)

(58) Field of Classification Search
None
See application file for complete search history.

(56) References Cited

FOREIGN PATENT DOCUMENTS

| WO | 03004498 A1 | 1/2003 | |
|----|----|----|----|
| WO | 2004080958 A2 | 9/2004 | |
| WO | 2004085378 A1 | 10/2004 | |
| WO | 2005020920 A2 | 3/2005 | |
| WO | 2005097733 A1 | 10/2005 | |
| WO | 2007050485 A2 | 5/2007 | |
| WO | 2009085990 A2 | 7/2009 | |
| WO | WO-2010122578 A2 * | 10/2010 | ........... C07D 209/48 |

OTHER PUBLICATIONS

Reichardt, Christian. Solvents and Solvent Effects in Organic Chemistry. 3rd ed. (2004) 418-421.*
Balsells et al., "Synthesis of [1,2,4] Triazolo [4,3-α] piperazines via Highly Reactive Chloromethyloxadiazoles", Organic Letters, 2005, vol. 7, No. 6, pp. 1032-1042.
European Search Report for Corresponding European Application No. EP 15191125. (dated Dec. 7, 2015) (3 Pages).

* cited by examiner

*Primary Examiner* — Deepak R Rao
*Assistant Examiner* — Laura M Daniel
(74) *Attorney, Agent, or Firm* — Lucas & Mercanti, LLP

(57) ABSTRACT

An improved process for the preparation of Triazole and salts thereof, a key intermediate for the synthesis of Sitagliptine is disclosed.

14 Claims, No Drawings

PROCESS FOR THE PREPARATION OF TRIAZOLE AND SALT THEREOF

TECHNICAL FIELD

The present invention relates to an improved process for the preparation of Triazole and salts thereof, a key intermediate for the synthesis of Sitagliptin.

BACKGROUND OF THE INVENTION

The compound Triazole, having the following chemical formula (II):

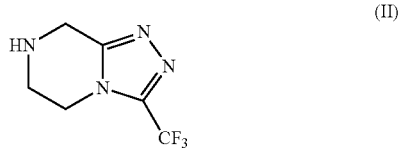 [SMILES: FC(F)(F)c1nnc2n1CCNC2]

has the chemical name 3-(trifluoromethyl)-5,6,7,8-tetrahydro[1,2,4]triazolo[4,3-a]pyrazine and CAS RN 486460-21-3.

Triazole is a key intermediate for the synthesis of Sitagliptin of formula (I):

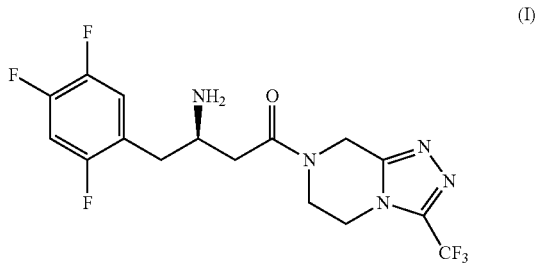 [SMILES: N[C@@H](CC(=O)N1CCn2c(nnc2C(F)(F)F)C1)Cc1cc(F)c(F)cc1F]

a substance also known as MK-0431 and having chemical name 7-[(3R)-3-amino-1-oxo-4-(2,4,5-trifluorophenyl)butyl]-5,6,7,8-tetrahydro-3-(trifluoromethyl)-1,2,4-triazolo[4,3-a] pyrazine. Sitagliptin is commercially available as the phosphate salt monohydrate under the trade name Januvia.

This active pharmaceutical ingredient is an oral antihyperglycemic (antidiabetic drug) of the dipeptidyl peptidase-4 (DPP-4) inhibitor. This enzyme-inhibiting drug is used alone or in combination with other oral antihyperglycemic agents, such as for example metformin or a thiazolidinedione, for treatment of diabetes mellitus type 2. The benefit of this medicine is its fewer side effects (e.g., less hypoglycemia, less weight gain) in the control of blood glucose values.

A synthetic process for the preparation of Sitagliptin is carried out by means of various steps, in particular one of them is the process for the preparation of Triazole.

A few methods for the preparation of Triazole have been disclosed.

In particular, Organic Letters, 7 (6), 1039-1042, 2005 discloses the synthesis of [1,2,4]Triazolo[4,3-r]piperazines via condensation of high reactive chloromethyloxadiazoles with ethylenediamins. The above mentioned article describes the preparation of different products, such as Oxadiazole, Triazole and substituted Triazoles. In particular, scheme 3, that is present in said article at page 1040, shows and briefly illustrates the preparation of Triazole 1a, starting from oxadiazole 3a proceeding to amidine 4a, thus to obtain 1a, through reflux of 4a in methanol. The experimental details, related to the preparation of 3-(trifluoromethyl)-5,6,7,8-tetrahydro[1,2,4]triazolo [4,3-a]pyrazine hydrochloride salt 1a, are not described in the same article, but they are disclosed in supporting information for [1,2,4]Triazolo[4,3-r]piperazines via condensation of high reactive chloromethyloxadiazoles at page 4.

Specifically, WO2004/080958 discloses, in example 1, in particular Step D, the preparation of 3-(trifluoromethyl)-5,6,7,8-tetrahydro[1,2,4]triazolo [4,3-a]pyrazine, hydrochloride salt (1-4), that was carried out by means of several steps with different solvents, and mostly with a substantial large amount of volumes, about 15 volumes.

In the above mentioned preparation, a warmed suspension of amidine in methanol (4V) was reacted with aqueous hydrochloric acid (37% HCl, 0.4V), producing a seed bed formed after the cooling. Later starting from the beforehand produced mixture, MTBE (11V) was added. The resulting slurry was cooled and filtered. Finally, for obtaining triazole 1-4, the solid cake was washed with ethanol:MTBE (1:3) solution (2V) and dried under vacuum at 45° C. In this method the conversion of amidine to triazole is carried out in methanol and water, while the isolation of the product is carried out from a mixture of methanol, water and MTBE.

The prior art methods this suffers of the drawbacks that the productivity of triazole is relatively low, especially considering the large volumes of solvents used, thus effecting the overall production capacity. Moreover, considering large productions, the recovery of the solvents is quite complex and require long cycling time.

SUMMARY OF THE INVENTION

The problem addressed by the present invention, in the light of the prior art methods, is therefore that of providing an improved process for the preparation of Triazole and salts thereof which allows one to increase the productivity and to avoid the needs of using different solvents, both for performing the conversion reaction and for isolating the product.

This problem is solved by a process for the preparation of Triazole and salts thereof as outlined in the annexed claims, whose definitions are integral part of the present description.

Particularly, the present invention provides a method for producing of Triazole of formula (II):

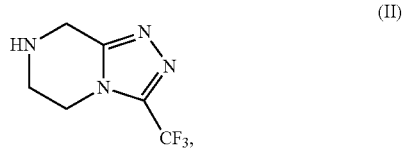 [SMILES: FC(F)(F)c1nnc2n1CCNC2]

a key intermediate in the synthesis process of active pharmaceutical ingredient Sitagliptin.

Said method comprises the conversion in acid environment of Amidine of formula (III):

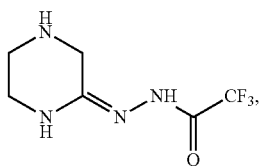

to compound of formula (II), wherein the conversion is carried out in ethanol, only; from thus obtained suspension of compound (II) in ethanol, the product of formula (II) is isolated.

Further features and advantages of the process according to the invention will result from the description hereafter reported of examples of realization of the invention, provided as an indication of the invention.

In a yet further aspect, the present invention provides a pharmaceutical composition comprising Sitagliptin or salt thereof, obtained by means of the Triazole prepared according process of the present invention, and one or more pharmaceutically acceptable excipients.

DETAILED DESCRIPTION OF THE INVENTION

An object of the present invention is a process for the preparation of Triazole of formula (II) and salt thereof:

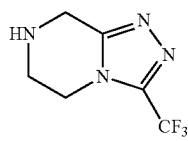

by means of the conversion in acid environment of Amidine of formula (III):

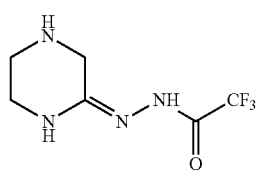

to compound of formula (II), wherein the conversion is carried out in ethanol, thus succeeding in lowering the amount of volumes used to carry out the conversions and to carry out the isolation of the product and, at the same time, avoiding the use of different solvents both in the conversion reaction and isolation of the product.

The produced suspension of compound (II) in ethanol indeed does not comprise any other solvent. Finally, the isolation of the product of formula (II) from the suspension of said compound is carried out in ethanol.

It has been indeed surprisingly found that the conversion in acid environment of Amidine of formula (III) to Triazole of formula (II) and salt thereof by means of ethanol allows a remarkable decrease of the volumes of solvent employed, thus dramatically improving the productivity of the process. The above mentioned reduction is performed using ethanol solvent instead of a mixture of methanol and water, as disclosed in prior art. Furthermore, such type of solvent, therefore employing ethanol rather than methanol and water, allows to carry out the process for the preparation of Triazole without the further addition of methyl tert-butyl ether (MTBE), as in the prior methods. The process described in prior art comprises the addition of MTBE for isolating Triazole, instead, the present invention allows one to produce Triazole without the use of MTBE or the other solvents, using ethanol, only. Therefore, the present invention describes a process for the preparation of Triazole (II) and salts thereof using only one solvent, which is ethanol, both for converting (III) to (II) and for isolating (II).

The lower of volumes of solvent used and the fact that only ethanol is used, produces the reduction of wastes. Moreover, said features of the process of the invention allow a strong increase of productivity and, at same time, a reduction production costs.

The present invention includes a process for the preparation of Triazole of formula (II) and salt thereof:

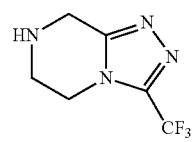

comprising the following steps:
a) conversion in acid environment of Amidine of formula (III):

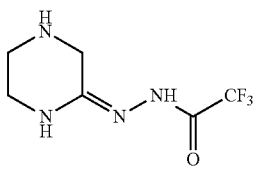

to compound of formula (II), wherein the conversion is carried out in ethanol,
b) obtaining suspension of compound (II) in ethanol,
c) isolation of the product of formula (II) from a suspension of said compound in ethanol.

According to a preferred embodiment of the present invention, the conversion of step a) is carried out in an acid environment, especially a solution of gaseous hydrochloric acid (HCl) on denatured ethyl alcohol is dosed to a mixture of Amidine of formula (III) and ethanol.

Besides, according to the above mentioned, the conversion is carried out in ethanol. This solvent is added to an amount of Amidine of formula (III) to produce a mixture of Amidine in ethanol.

The mixture of Amidine and ethanol is heated at a temperature of between 55° C. and 65° C., and preferably at a temperature about 60° C.

The heated mixture is dosed with a solution of gaseous hydrochloric acid on denatured ethanol to convert the Amidine of formula (III) to Triazole (II), and thus to produce a suspension of the compound of formula (II).

Said suspension or slurry is an amount of solid material of the compound of formula (II) suspended in ethanol.

The process of the invention is carried out using ethanol as solvent, therefore the suspension of the product of formula (II) is in ethanol, only.

According to a preferred embodiment, wherein the suspension of compound (II) of the step b) is obtained in ethanol, in particular said suspension is carried out without the addition of any other solvent.

In step a) is a previously prepared suspension of the compound of formula (III) in ethanol which is then heated at 55-65° C., after the addition of the acid, then the mixture is heated at reflux, in particular it is warmed at a temperature about 79° C.

The mixture is kept at about 79° C. for at least 30 minutes.

Then the resulting slurry is cooled at room temperature, purposely at temperature between from 20° C. to 25° C.

Therefore, according to the above, the suspension of compound (II) of step b) is obtained in ethanol, after stirring, without the addition whatever solvent, specifically without the addition of methyl tert-butyl ether (MTBE), as instead of that disclosed in prior art.

According to a preferred embodiment, in step b) of the process for the preparation of Triazole of formula (II) and salt thereof of the present invention, the suspension of compound (II) in ethanol is obtained without a the addition of any other solvent.

According to a preferred embodiment of the process of the present invention, step a) and/or step b) is carried out without the addition of water.

Specifically, according to a more preferred embodiment of the process of the present invention, step a) is carried out without the addition of water or step b) is carried out without the addition of water or both steps a) and b) are carried out without the addition of water.

According to another preferred embodiment of the present invention, step a) or step a) and step b), ethanol contains an amount of water lower than 0.10 volumes compared to the compound of formula (III); more preferably ethanol contains an amount of water of about 0.05 volumes as compared to the same compound of formula (III).

As for definition, 1 volume of solvent is an amount of volume per amount of substance. For example 1 volume can be 1 Liter per 1 Kilogram or 1 mL per 1 gram, 1 microliter per 1 microgram, etc.

According to a preferred embodiment of the present invention, both steps a) and b) are carried out at an amount of volumes of ethanol between about 1 and about 6 volumes as compared to the compound of formula (III).

According to a more preferred embodiment of the present invention, wherein both steps a) and b) are carried out at an amount of volumes of ethanol between about 1.5 and about 2.0 volumes compared to the compound of formula (III), more preferably said steps are carried out at about 1.7 volumes of ethanol.

The process of the invention provides Triazole with a molar yield between from about 89.00% to 90.70%, and a HPLC purity more than 99.7% A/A %.

Finally, starting from the suspension of the compound of the step b) in ethanol, in the step c), Triazole of formula (II) and salt thereof is isolated, by means of a filtration or centrifugation, preferably by filtration, and then the cake is washed with ethanol and then the solid is discharged and dried under vacuum at a temperature about 50° C.

The process of the presence invention allows the preparation of the following Triazole of formula (II):

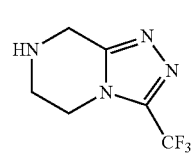

(II)

and salts thereof, for example, sulphate, hydrobromide, nitrate salt, etc., preferably the hydrochloride salt having the following structure:

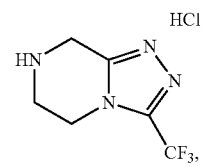

Another aspect of the present invention is the use of ethanol for the conversion of Amidine of formula (III):

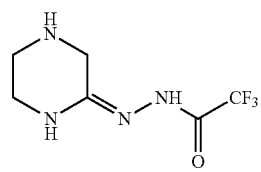

(III)

to Triazole of formula (II) and salts thereof:

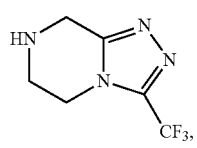

(II)

thus obtaining suspension of compound (II) in ethanol.

In particular, said conversion is carried out in ethanol, as beforehand described, the mixture, made up an amount of Amidine of formula (III) in ethanol, reacts in presence of gaseous hydrochloric acid to obtain a suspension of compound (II) and salt thereof, in ethanol.

A further aspect of the invention is the process for the preparation of Sitagliptin of formula (I) and salt thereof:

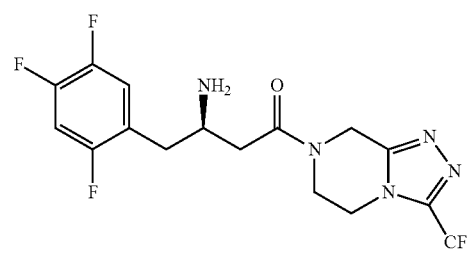

(I)

consisting of the following steps:

A) conversion of Amidine of the formula (III) to Triazole of formula (II) and salt thereof according the process of the present invention, B) conversion of Triazole of the step A) to obtain Sitagliptin.

The conversion of the step A) have been described above in the paragraphs describing the process for preparation of Triazole of formula (II) and salt thereof.

Starting from the same Triazole of formula (II), by means of conversion of the step B), Sitagliptin of formula (I) and salts thereof are obtained, since the product (II) is a key intermediate in the process for the synthesis of the same Sitagliptin.

According to a preferred embodiment of the invention, the process for the preparation of Sitagliptin of formula (I) and salts thereof, wherein step B) is carried out by means of the following steps:

C) the conversion of Triazole to Ketoamide of formula (IV)

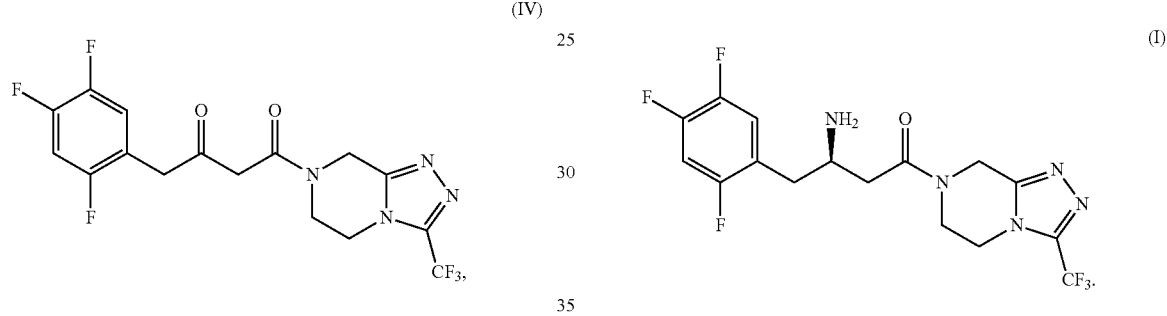

D) the reaction to produce Enamine Amide of formula (V) from Ketoamide, produced in the step C)

(V)

E) the conversion of Enamine Amide of step D) to Sitagliptin of formula (I):

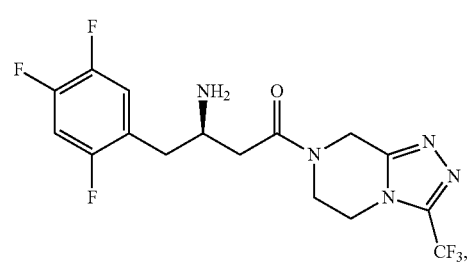

(I)

or by means the alternative process for obtaining Sitagliptin, wherein the steps C), D) and E) are substituted by the following steps:

C1) the conversion of Triazole to Ketoamide of formula (IV):

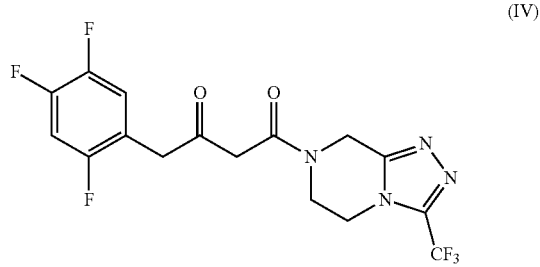 [SMILES: O=C(CC(=O)N1CCn2c(nnc2C(F)(F)F)C1)Cc1cc(F)c(F)cc1F]

D1) the enzymatic conversion of Ketoamide of formula (IV), obtained by previous step C1), to Sitagliptin of formula (I):

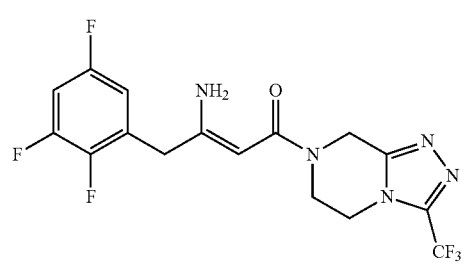

(I)

In particular, Ketoamide of formula (IV) of step C) and the same Ketoamide of step C1) are produced according to the known prior art methods, such as those disclosed in WO2005/020920, the disclosure of which is incorporated herein by reference, purposely in Step A, related to scheme 2 of example 1.

Then, following the process, the reaction to produce Enamine Amide of formula (V) from Ketoamide, produced in the step C) and the conversion of Enamine Amide of step D) to Sitagliptin of formula (I) are disclosed respectively in Step B and in Step C, related to scheme 2, of WO2007/050485, the disclosure of which is incorporated herein by reference.

An alternative process for obtaining Sitagliptin, starting from Ketoamide of formula (IV), beforehand described, includes the enzymatic conversion of the same Ketoamide, obtained by previous step C1), to Sitagliptin of formula (I). This enzymatic conversion is disclosed in the known prior art, in particular in the article of Science, 2010, volume 329, pp. 305-309, the disclosure of which is incorporated herein by reference.

In one embodiment of the present invention, Sitagliptin of formula (I) or salt thereof, prepared according to the above process, may be included in pharmaceutical compositions, comprising one or more pharmaceutically acceptable excipients or in combination with other active pharmaceutical ingredients and one or more pharmaceutically acceptable excipients.

Example of suitable pharmaceutical composition, in particular in combination with other active pharmaceutical ingredients, is a tablet comprising 50 mg of Sitagliptin (as phosphate monohydrate salt) and 850 mg of metformin hydrochloride.

Other examples suitable pharmaceutical compositions are following described:
25 mg tablet contains sitagliptin phosphate monohydrate, equivalent to 25 mg sitagliptin,
50 mg tablet contains sitagliptin phosphate monohydrate, equivalent to 50 mg sitagliptin,
100 mg tablet contains sitagliptin phosphate monohydrate, equivalent to 100 mg sitagliptin,
wherein the above pharmaceutical compositions contain the following excipients in tablet core: microcrystalline cellulose (E460), calcium hydrogen phosphate, anhydrous (E341), croscarmellose sodium (E468), magnesium stearate (E470b) and sodium stearyl fumarate.

Furthermore the film coating of the said pharmaceutical compositions can be made up the following excipients: poly(vinyl alcohol), macrogol 3350, talc (E553b), titanium dioxide (E171), red iron oxide (E172) and yellow iron oxide (E172).

In one embodiment of the present invention, Sitagliptin of formula (I) or a salt thereof, prepared according to the above process, or pharmaceutical compositions comprising Sitagliptin alone or combination with other active pharmaceutical ingredients and one or more pharmaceutically acceptable excipients, can be suitable for use in medicine.

Specifically, in one preferred embodiment of the present invention, Sitagliptin of formula (I) or salt thereof, prepared according to the above process, or pharmaceutical compositions comprising Sitagliptin alone or combination with other active pharmaceutical ingredients and one or more pharmaceutically acceptable excipients, can be suitable for use in the treatment of diabetes mellitus type 2. Such treatment is carried out by administering an effective amount of sitagliptin prepared according to the processes described herein to a patient in need thereof. The amount of sitagliptin administered will be apparent to those of ordinary skill in the art without undue experimentation. For example, such effective amounts are typically from about 25 mg to about 100 mg or more given once daily.

According to another embodiment for the preparation of Triazole of formula (II) and salts thereof of the present invention, the conversion of step a) is carried out by means of aqueous hydrochloric acid as an alternative to the gaseous hydrochloric acid (HCl).

According to a preferred embodiment of the present invention, the conversion of step a) is carried out by means of aqueous hydrochloric acid wherein the volumes of aqueous hydrochloric acid are from 0.1 to 1 volume compared to the compound of formula (III); more preferably the volume of aqueous hydrochloric acid is 0.5 volumes compared to the compound of formula (III).

According to a preferred embodiment of the present invention, the conversion of step a) is carried out by means of aqueous hydrochloric acid wherein the concentration of aqueous hydrochloric acid is from 32 to 37 wt %.

According to a more preferred embodiment of the present invention, the conversion of step a) is carried out by means of aqueous hydrochloric acid wherein the volumes of aqueous hydrochloric acid are from 0.1 to 1 volume compared to the compound of formula (III), and the concentration of aqueous hydrochloric acid is from 32 to 37 wt %.

Those skilled in the art of organic chemistry can appreciate that the process of the invention allows for a dramatic improvement in productivity, considering the strong reductions of volumes employed to carry out both conversion and isolation of the product from maximum volumes of about 15 volumes to about 1.7 volumes, at the same time, avoiding the use of solvent mixtures.

Regarding to the concept of productivity of a process, it is intended to be the output in terms of Kgs of product per hours or per batch.

It has to be considered that the volume of an (industrial) reactor is a fixed parameter, for example 20 liters, therefore if the reaction and workup occurs for example in only 1.7 volumes of solvent, and assuming a yield of 100% by weight, the output for batch will be about =20/(1+1.7)=ca. 7.4 Kg, wherein if it occurs in 15 volumes (as disclosed in Organic Letters, 7 (6), 1039-1042, 2005) the output will be only 1.25 kg.

Thus, the distinguishing feature of the invention, i.e. ethanol, instead of methanol+MTBE, provides the effect of strong increase of the productivity, since as just explained, the productivity is much higher with the process of the invention in comparison with the optimized process of the above mentioned Organic Letters or with other process of the prior art.

EXPERIMENTAL SECTION

The starting material Amidine can be produced according to the known prior art methods, such as those disclosed in WO2005/020920 or WO2005/097733 or WO2007/050485, the disclosure of each of which is incorporated herein by reference.

Example 1: Preparation of Triazole of Formula (II) as HCl Salt in 5 Volumes of Ethanol with the Presence Catalytic Amount of Water

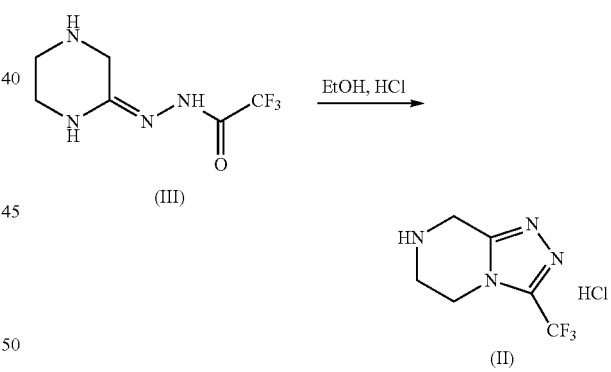

Into a three necked round bottom flask, under nitrogen atmosphere, 250 g of Amidine of formula (III), 1000 mL of denatured ethanol (4V) and 12.5 mL of water (0.05V). The obtained suspension is heated at temperature 60° C. and stirring at the same temperature at least 15 min. Then a solution of 45 g HCl (gas) in 250 mL denatured ethanol (1V) was dosed in 20 min., keeping the temperature at temperature range from 55° C. to 60° C. The resulting mixture was stirred for 1 hour at the same temperature. The slurry was cooled at room temperature and was stirred for least 30 min. at the same temperature. The obtained slurry was filtered and the solid was washed with 250 mL of denatured ethanol. Drying the solid under vacuum at T=45° C., 246.25 g of Triazole of formula (II) as HCl salt were obtained with 90.53% of molar yield.

Example 2: Preparation of Triazole of Formula (II) as HCl Salt in 1.7 Volumes of Ethanol

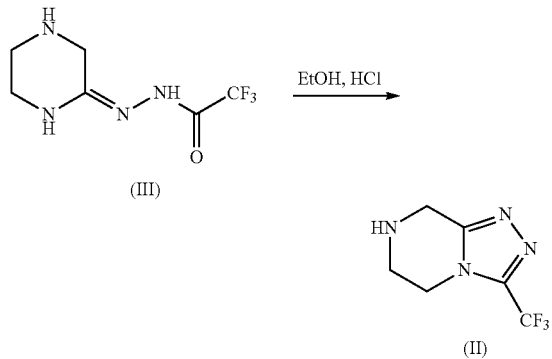

Into a three necked round bottom flask, under nitrogen atmosphere, 500 g of Amidine of formula (III), 450 mL of denatured ethanol (0.9V). The obtained suspension is heated at temperature 60° C. and stirring at the same temperature at least 15 min. Then a solution of 90 g HCl (gas) in 315 mL denatured ethanol (0.8V) was dosed in 20 min., keeping the temperature at temperature range from 55° C. to 60° C. The resulting mixture was stirred for 1 hour at the same temperature. The slurry was cooled at room temperature and was stirred for least 30 min. at the same temperature. The obtained slurry was filtered and the solid was washed with 500 mL of denatured ethanol. Drying the solid under vacuum at T=45° C., 493.5 g of Triazole of formula (II) as HCl salt were obtained with 90.71% of molar yield.

Example 3: Preparation of Triazole of Formula (II) as HCl Salt in 1.7 Volumes of Ethanol

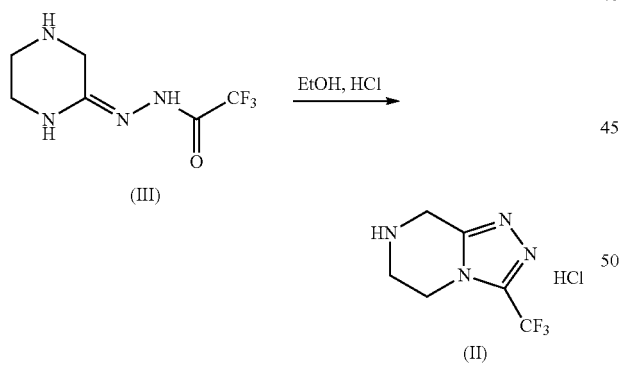

Into a three necked round bottom flask, under nitrogen atmosphere, 180 g of Amidine of formula (III) and 180 mL of denatured ethanol (1V). The obtained suspension is heated at temperature 60° C. and stirring at the same temperature at least 15 min. 122.1 g of a solution of HCl (gas) on denatured ethanol (0.7V) were dosed for 20 min., keeping the temperature at temperature range from 60° C. to 70° C. The resulting mixture was heated a reflux (T=79° C.) for 30 min. The slurry was cooled at room temperature and was stirred for least 30 min. at the same temperature. The obtained slurry was filtered washing the solid with 180 mL of denatured ethanol. Drying the solid under vacuum at T=50° C., 175.7 g of Triazole of formula (II) as HCl salt were obtained with 89.94% of molar yield and HPLC purity of 99.8% A/A %.

Example 4: Preparation of Triazole of Formula (II) as HCl Salt in 1.7 Volumes of Ethanol

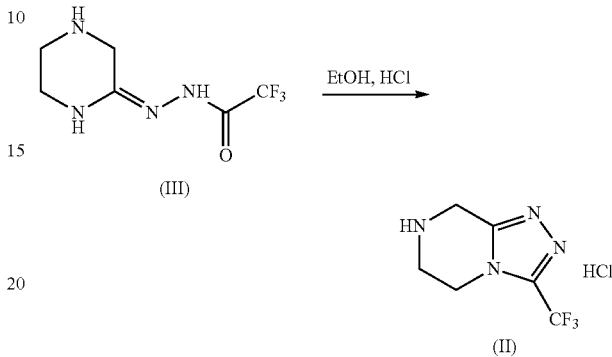

Into a three necked round bottom flask, under nitrogen atmosphere, 180 g of Amidine of formula (III) and 180 mL of denatured ethanol (1V). The obtained suspension is heated at temperature 60° C. and stirring at the same temperature at least 15 min. 122.1 g of a solution of HCl (gas) on denatured ethanol (0.7V) were dosed for 20 min., keeping the temperature in a range from 60° C. to 70° C. The resulting mixture was heated a reflux (T=79° C.) for 30 min. The slurry was cooled at room temperature and was stirred for least 30 min. at the same temperature. The obtained slurry was filtered washing the solid with 180 mL of denatured ethanol. Drying the solid under vacuum at T=50° C., 176.6 g of Triazole of formula (II) as HCl salt were obtained with 90.20% of molar yield and HPLC purity of 99.8% A/A %.

The invention claimed is:
1. A process for the preparation of a triazole of formula (II) and salts thereof:

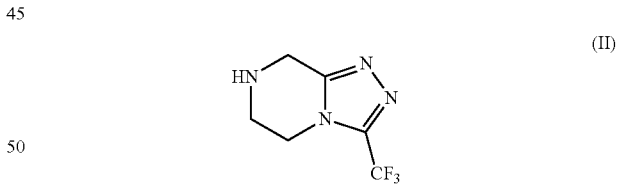

comprising:
a) converting an amidine of formula (III):

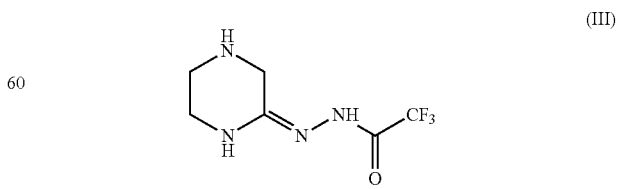

in an acid environment to form the triazole of formula (II), wherein the converting is carried out in ethanol, b) obtaining a suspension of the triazole of formula (II) in ethanol, without the addition of any other solvent, and c) isolating the triazole of formula (II) from the suspension of the triazole of formula (II) in ethanol.

2. The process according to claim 1, wherein step a) or step b) is carried out without the presence of water.

3. The process according to claim 1, wherein in step a) or in both steps a) and b) the ethanol contains an amount of water lower than 0.10 volumes compared to the amidine of formula (III).

4. The process according to claim 1, wherein both steps a) and b) are carried out in ethanol between 1 and 6 volumes compared to the amidine of formula (III).

5. The process according to claim 1, wherein the volumes of ethanol are between 1.5 to 2.0 volumes compared to the amidine of formula (III).

6. The process according to claim 1, wherein the converting in step a) is carried out by means of gaseous hydrochloric acid.

7. The process according to claim 1, wherein the converting in step a) is carried out by means of aqueous hydrochloric acid.

8. The process according to claim 7, wherein the volumes of aqueous hydrochloric acid are between from 0.1 to 1 volume compared to the compound of formula (III).

9. The process according to claim 7, wherein the concentration of aqueous hydrochloric acid during the converting in step a) is from 32 to 37% w/w.

10. A process for the preparation of sitagliptin of formula (I) and salts thereof:

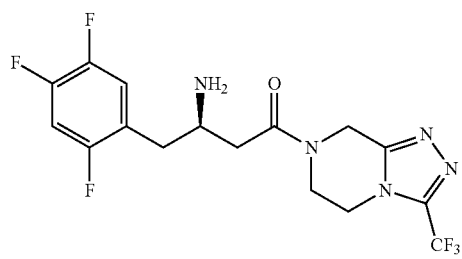

comprising:
a) converting an amidine to a triazole according to the process of claim 1, and
b) converting the triazole of step a) to obtain sitagliptin.

11. The process according to claim 10, wherein step b) is carried out by:
c) converting the triazole to a ketoamide of formula (IV):

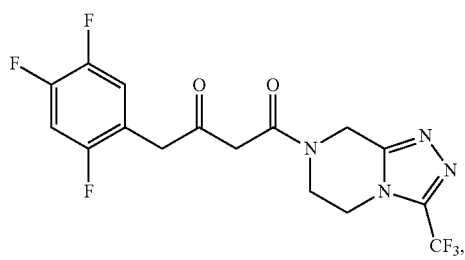

d) producing the enamine amide of formula (V) from the ketoamide produced in step c):

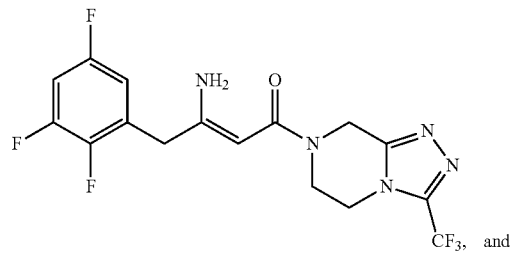

e) converting the enamine amide of step d) to sitagliptin of formula (I):

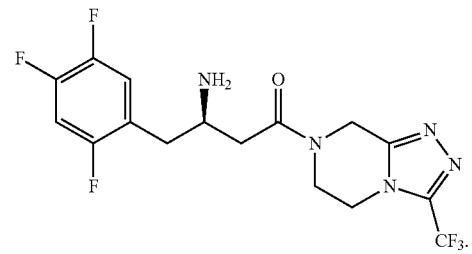

12. The process according to claim 10, wherein step b) is carried out by:
c) converting the triazole to a ketoamide of formula (IV):

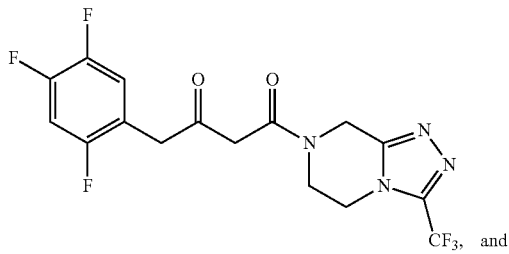

d) enzymatically converting the ketoamide of formula (IV) obtained in step c) to sitagliptin of formula (I):

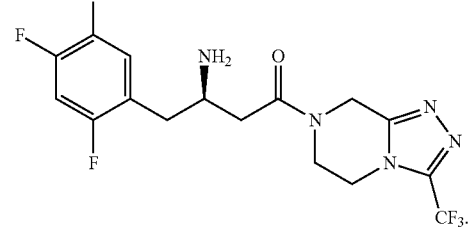

13. The process according to claim 1, wherein both steps a) and b) are carried out without the presence of water.

14. A process for the preparation of a triazole of formula (II) and salts thereof:

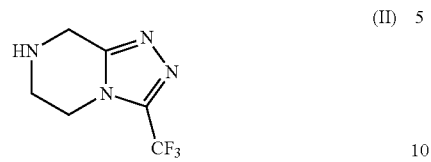

comprising:
a) converting an amidine of formula (III):

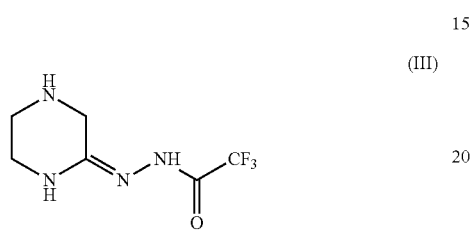

in an acid environment to form the triazole of formula (II), wherein the converting is carried out in a solvent consisting of ethanol,
b) obtaining a suspension of the triazole of formula (II) in the solvent consisting of ethanol, and
c) isolating the triazole of formula (II) from the suspension.

* * * * *